United States Patent
Ho et al.

(10) Patent No.: US 10,198,937 B2
(45) Date of Patent: Feb. 5, 2019

(54) SYSTEMS, DEVICES, AND METHODS FOR REMOTELY INTERROGATED CHEMOSENSOR ELECTRONICS

(71) Applicant: Raytheon BBN Technologies Corp., Cambridge, MA (US)

(72) Inventors: John Ho, Cambridge, MA (US); Thomas Patrick Bidigare, Arlington, VA (US)

(73) Assignee: Raytheon BBN Technologies Corp., Cambridge, MA (US)

( * ) Notice: Subject to any disclaimer, the term of this patent is extended or adjusted under 35 U.S.C. 154(b) by 50 days.

(21) Appl. No.: 15/006,827

(22) Filed: Jan. 26, 2016

(65) Prior Publication Data

US 2016/0140838 A1    May 19, 2016

Related U.S. Application Data

(63) Continuation of application No. 12/840,452, filed on Jul. 21, 2010, now abandoned.

(Continued)

(51) Int. Cl.

| | |
|---|---|
| G08C 17/02 | (2006.01) |
| G01N 21/64 | (2006.01) |
| G01N 21/77 | (2006.01) |
| G08B 5/22 | (2006.01) |
| G08B 21/12 | (2006.01) |

(52) U.S. Cl.
CPC ......... *G08C 17/02* (2013.01); *G01N 21/6428* (2013.01); *G01N 21/77* (2013.01); *G08B 5/22* (2013.01); *G08B 21/12* (2013.01)

(58) Field of Classification Search
None
See application file for complete search history.

(56) References Cited

U.S. PATENT DOCUMENTS

| 5,597,534 A | 1/1997 | Kaiser |
|---|---|---|
| 7,208,122 B2 | 4/2007 | Swager et al. |

(Continued)

OTHER PUBLICATIONS

Akliouat, H. et al. Synthetic Aperture Radar Image Formaton Process: Application to a Region of North Algeria, Proc. Envisa Symposium 2007, Montreux, Switzland, Apr. 23-27, 2007.*

(Continued)

*Primary Examiner* — Xiaoyun R Xu
(74) *Attorney, Agent, or Firm* — Lando & Anastasi, LLP

(57) ABSTRACT

Systems, devices and methods for remotely interrogating sensor electronics are described. In one embodiment, a system for detecting and localizing chemical analytes is described. This system includes a plurality of chemosensor electronic devices for detecting the presence of chemical analytes. Each of these devices includes a chemosensor for sensing chemical analytes, a transponder, and an electronic circuit for activating the transponder based on an output of the chemosensor. These devices may have a cross-section area of less than 1 square micrometer. The system also includes an interrogation device for interrogating the plurality of devices and for receiving information on the detected chemical analytes from devices with activated transponders, and a processor for determining the locations of the devices with activated transponders. These locations may be forwarded to a third party.

20 Claims, 11 Drawing Sheets

Related U.S. Application Data

(60) Provisional application No. 61/227,244, filed on Jul. 21, 2009.

(56) References Cited

U.S. PATENT DOCUMENTS

| | | |
|---|---|---|
| 7,393,503 B2 | 7/2008 | Swager et al. |
| 2007/0126576 A1* | 6/2007 | Script ............... G01P 13/00 340/545.5 |

OTHER PUBLICATIONS

Ho, John C., "Organic Lateral Heterojunction Devices for Vapor-phase Chemical Detection", Submitted to the Department of Electrical Engineering and Computer Science on May 21, 2009, Massachusetts Institute of Technology, pp. 1-252.

Ho, J. et al., "Solid-State Chemosensitive Organic Devices for Vapor-Phase Detection," Organic Semiconductors in Sensor Applications, Springer Series in Material Science, 107:141-184 (2008).

* cited by examiner

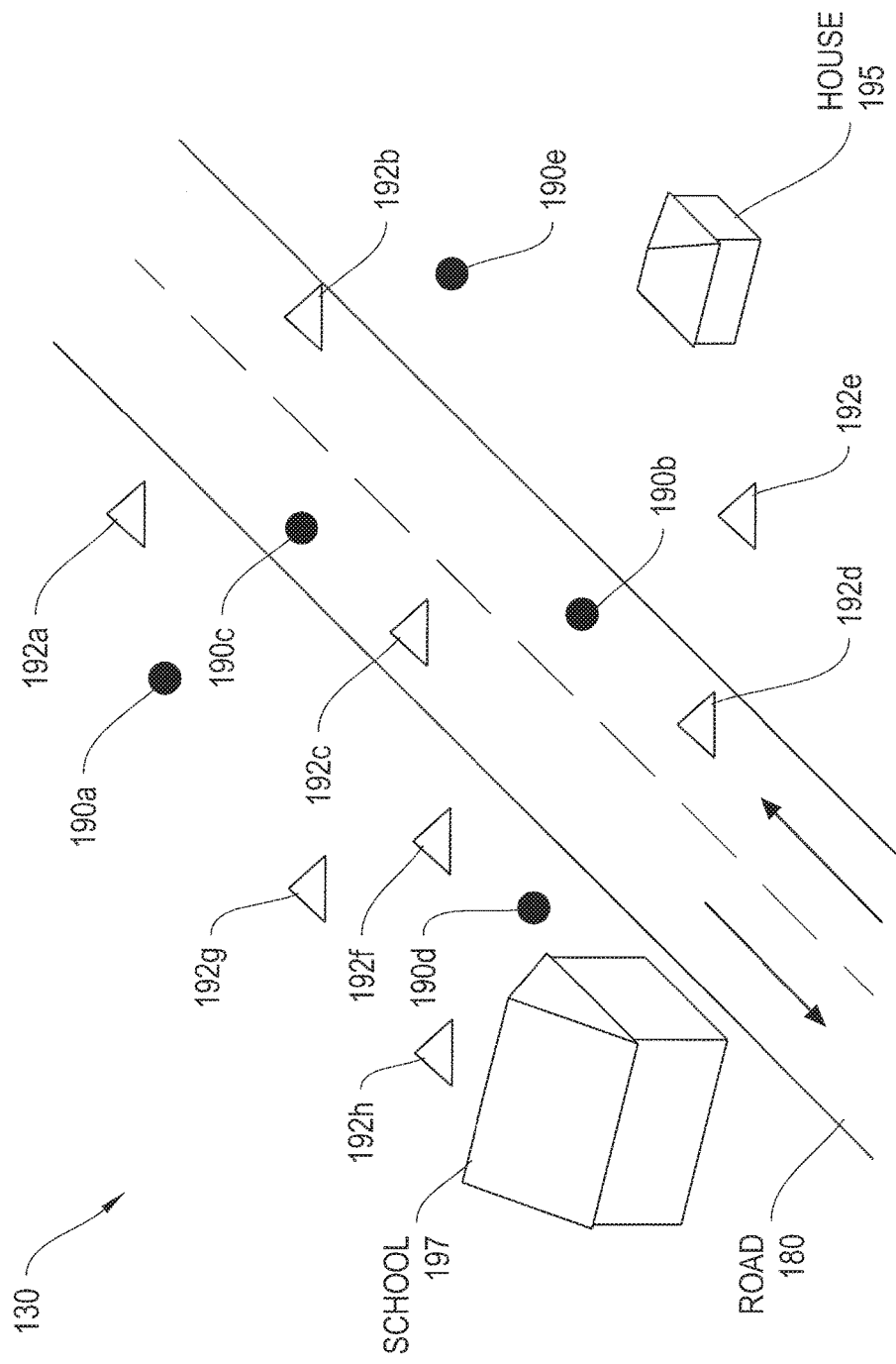

SYSTEMS, DEVICES, AND METHODS FOR REMOTELY INTERROGATED CHEMOSENSOR ELECTRONICS

CROSS-REFERENCE TO RELATED APPLICATIONS

This application is a continuation application of U.S. patent application Ser. No. 12/840,452, filed Jul. 21, 2010, which claims priority to U.S. Provisional Patent Application No. 61/227,244, filed Jul. 21, 2009. The aforementioned, earlier-filed applications are hereby incorporated by reference in their entireties.

FIELD OF THE INVENTION

This disclosure relates generally to chemical detection, and more particularly, the methods, systems and devices disclosed herein relate to portable high-sensitivity high-specificity long-standoff distance methods, systems and devices for the detection and localization of vapor-phased explosives, illegal drugs, hazardous waste, bioagents, or other chemical analytes.

BACKGROUND

The long standoff detection or sensing of chemical analytes is important in many applications. In the policing of borders and reduction or elimination of illegal drug trafficking, the detection of chemical constituents from a large distance associated with illegal drugs can help identify smuggling routes and perpetrators. The detection of these chemicals could drastically improve the border patrol's effectiveness. In biochemical warfare, the detection or sensing of hazardous bioagents from afar is also of high importance in order to provide early warning and identify proper countermeasures. In today's war zones, the detection or sensing of vapor-phase explosives with high-sensitivity is of utmost importance, particularly, because in many war zones, the use of improvised explosive devices (IEDs) have resulted in a large number of deaths, e.g., more than 50% of all coalition deaths in Iraq and Afghanistan. These deaths could be significantly reduced if it was possible to accurately detect the presence of these IEDs from a distance without jeopardizing the lives of human investigators.

Most commercially-available chemical sensing devices or systems have several drawbacks. First, these devices and systems generally require skilled human operators, making it difficult to deploy these devices or systems remotely and/or autonomously. Second, these systems and devices generally only provide chemical detection capability over a limited geographical area and are not amenable to wide area scanning. Third, these chemical detection devices are generally too large and/or heavy to be used for covert operations.

Vapor-phase explosives detection technology has emerged as one of the most sensitive tools in the military's explosives detecting arsenal. In these so-called "sniffing" explosives detection devices, e.g., the FIDO™ XT portable explosives detector (available from ICx Technologies, Mass.), the detection of the chemicals/explosives is based on the attachment of specific, known chemicals/explosives to fluorescent polymers. The fluorescence of these polymers is dependent on the binding of specific chemical analytes to the polymers. For example, an explosive may cause a reduction in fluorescence of the polymers. The polymer is excited by light from a light emitting diode (LED) or laser. These fluorescent polymers have the property that their photoluminescence becomes quenched as vapor-phase chemicals bind to the surface of the fluorescent polymer. The reduced fluorescence of the polymer film is detected by a photodetector to generate an electrical current signal.

Despite their demonstrable success, portable explosives detection devices such as the Fido™ XT also have several drawbacks. First, in devices such as the FIDO™ XT, there are significant optical losses in the transmission of photons from the fluorescent polymer to the photodetector, yielding inefficient chemical to electrical signal transduction. These detection devices are difficult to miniaturize because efficient isolation of optical signals with similar wavelengths is difficult if one wishes to have a small micrometer-scale device. In particular, the micro-fabrication of closely packed fluorescent polymer layers with similar fluorescence spectra can be problematic due to the difficulty in isolating the optical signal from each element. Of particular relevance, commercially-available chemical detectors cannot be deployed remotely as they do not have any remote interrogation capabilities, and due to their size, typically are deployed in the field with a skilled user, thereby putting lives at risk. In particular, commercially-available chemical detection systems and devices are not capable of being interrogated from large distances, e.g., a few km, making them unusable for covert detection applications, and greatly limiting the area over and speed with which chemical analytes can be found.

SUMMARY

There exists a need for a chemical detection and localization device which can be remotely interrogated, thereby eliminating the need for a skilled user to accompany the device into the field. There also exists a need for a chemical detection and localization device that can multiplex the detection signals from an array of fluorescent polymer sensors while maintaining high sensitivity and high specificity.

The methods, systems and devices described herein address these and other needs. Among other things, the methods, systems and devices described herein address the inefficient chemical to electrical signal transduction process described above with respect to commercially-available chemical sensors/detectors. They add the ability to remotely interrogate such chemical detectors. In addition, they enable the miniaturization of chemical sensors/detectors, thereby allowing widespread deployment of chemical sensors/detectors in covert operations and in distributed applications.

In one aspect, the invention relates to a device for detecting chemical analytes. The device includes a chemosensor for sensing chemical analytes. The chemical analytes include one of vapor-phase explosives, illegal drugs, hazardous waste, and bioagents. The device also includes a transponder for receiving an interrogation signal from a remote interrogation device and transmitting a signal to the remote interrogation device in response to the received interrogation signal. The device further includes an electronic circuit for activating the transponder based on an output of the chemosensor. In some embodiments, the chemosensor includes a Type-II bilayer heterjunction, and this junction includes a fluorescent polymer layer and a conductive metal oxide layer. In some embodiments, the chemosensor has a cross-section area less than 1 square micrometer. In some embodiments, the transponder is a radar transponder. In some embodiments, the remote interrogation device is located at least 250 m from the transponder of the device.

In another aspect, the invention relates to a method for detecting chemical analytes. The chemical analytes include one of vapor-phase explosives, illegal drugs, hazardous waste, and bioagents. The method includes sensing chemical analytes using a chemosensor, receiving an electrical signal from the chemosensor, activating a transponder based on the received electrical signal, receiving an interrogation signal at the transponder from a remote interrogation device, and transmitting a signal from the transponder to a remote interrogation device in response to the received interrogation signal. In some embodiments, the chemosensor includes a Type-II bilayer heterjunction, and this junction includes a fluorescent polymer layer and a conductive metal oxide layer. In some embodiments, the chemosensor has a cross-section area less than 1 square micrometer. In some embodiments, the transponder is a radar transponder. In some embodiments, the remote interrogation device is located at least 250 m from the transponder.

In a third aspect, the invention relates to a method for the detection and localization of chemical analytes. The chemical analytes include one of vapor-phase explosives, illegal drugs, hazardous waste, and bioagents. The method includes deploying a plurality of chemosensor electronic devices in an area to detect the presence of the chemical analytes in the area and activating a transponder in a respective device if analytes are detected by the respective device. The method also includes interrogating the plurality of devices to receive information on the detected analytes from devices with activated transponders, and determining the locations of the devices with activated transponders. The method includes forwarding the determined locations to a third party in response to this determination. In some embodiments, the chemosensor includes a Type-II bilayer heterjunction, and this junction includes a fluorescent polymer layer and a conductive metal oxide layer. In some embodiments, the chemosensor has a cross-section area less than 1 square micrometer. In some embodiments, the transponder is a radar transponder. In some embodiments, the remote interrogation device is located at least 250 m from the transponder.

In a fourth aspect, the invention relates to a system for detecting and localizing chemical analytes. The chemical analytes include one of vapor-phase explosives, illegal drugs, hazardous waste, and bioagents. The system includes a plurality of chemosensor electronic devices for detecting the presence of the chemical analytes, wherein each device includes a transponder that can be activated based on the detected chemical analytes. The system further includes an interrogation device. The interrogation device is for interrogating the plurality of devices, and receiving information on the detected chemical analytes from devices with activated transponders. The system further includes a processor. The processor is for determining the locations of the devices with activated transponders, and for forwarding the determined locations to a third party. In some embodiments, the chemosensor includes a Type-II bilayer heterjunction, and this junction includes a fluorescent polymer layer and a conductive metal oxide layer. In some embodiments, the chemosensor has a cross-section area less than 1 square micrometer. In some embodiments, the transponder is a radar transponder. In some embodiments, the remote interrogation device is located at least 250 m from the transponder.

BRIEF DESCRIPTION OF DRAWINGS

The following figures depict certain illustrative embodiments of the invention in which like reference numerals refer to like elements. These depicted embodiments may not be drawn to scale and are to be understood as illustrative of the invention and as not limiting in any way:

FIG. 1B is a detection map that may be generated by an interrogation device using an image formation algorithm, according to an illustrative embodiment of the invention;

DETAILED DESCRIPTION OF ILLUSTRATIVE EMBODIMENTS

To provide an overall understanding of the invention, certain illustrative embodiments will now be described, including exemplary remotely interrogated chemosensor electronics (RICE) devices and constituent components thereof. However, it will be understood by one of ordinary skill in the art that the apparatus described herein may be adapted and modified as is appropriate for the application being addressed and that the systems and methods described herein may be employed in other suitable applications, and that such other additions and modifications will not depart from the scope hereof.

In one embodiment, the chemical detection device is a miniature, remotely interrogated chemosensor electronics (RICE) device. In general, RICE devices can be deployed for any chemical sensing application, including the detection or sensing of vapor-phase explosives in a battlefield, illegal drugs in a border region, or the detection or sensing of hazardous bioagents in an urban region, as described further with respect to FIGS. 1A-1C. Illustrative embodiments of RICE devices, methods for detecting chemical analytes using a RICE device, and RICE device designs are described below with respect to FIGS. 2A-6.

Figure 1A:
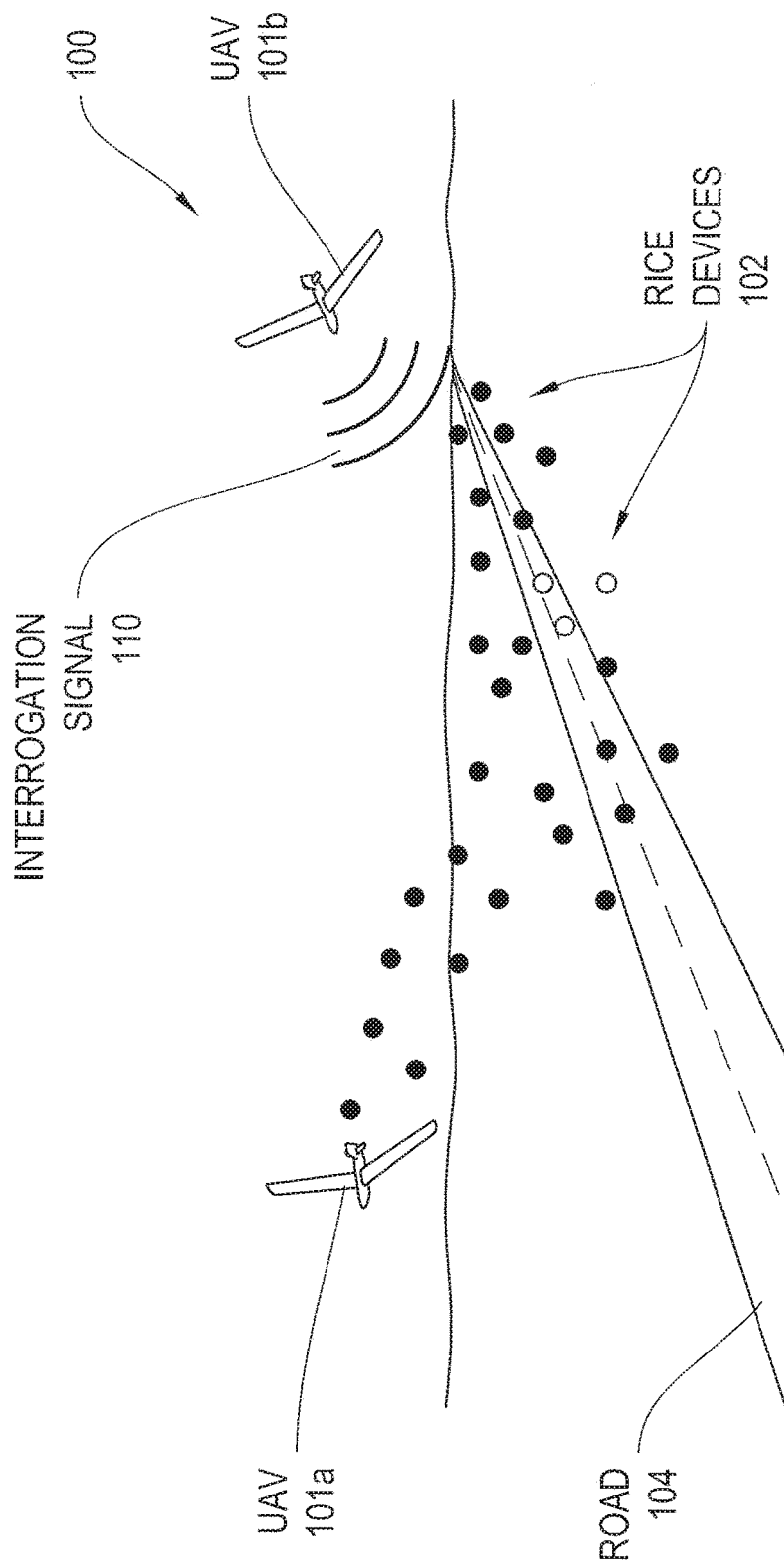
FIG. 1A is an application of several remote interrogation chemosensor devices in an area, according to an illustrative embodiment of the invention.

FIG. 1A shows an illustrative application of RICE devices 102 for detecting and localizing chemical analytes. In the illustrative application, RICE devices 102 are deployed in an area 100 with a road 104. The RICE devices 102 are deployed by scattering the devices on the road 104 using a manned or unmanned vehicle such as UAV 101a, an aircraft or a ground vehicle. Once deployed, RICE devices 102 are remotely interrogated via an interrogation signal 110, e.g., a radar signal, emanating from an interrogation device such as a second UAV 101b or other aircraft. In one embodiment, the same aircraft, UAV, or ground vehicle is used for deployment and interrogation. If chemical analytes, e.g., vapor-phase explosives, are detected by the RICE devices 102, each RICE device 102 detecting the chemical analytes transmits a signal representative of the type and/or level of chemicals detected by the RICE device. RICE devices that detect chemical analytes are referred to as being "activated."

Once a signal transmitted by a RICE device is received at the interrogation device, the location of the RICE device can be determined using a localization algorithm such as a synthetic aperture radar (SAR) image formation algorithm. In one embodiment, the resulting SAR image may be a combination of the locations of many RICE devices in a particular area, from which one may create a map representative of the location, concentration, and type of chemicals detected. In another embodiment, the resulting SAR image may be used for its location information alone.

FIG. 1B is a detection map 130 that may be generated by an interrogation device using a SAR image formation algorithm based on data obtained from RICE devices distributed in an area, such as RICE devices 102 of FIG. 1A. Map 130 includes a road 180, house 195, and school 197. The map also includes indications of observed chemical analytes. Specifically, the presence of a first type of chemical is indicated by the circles on the map corresponding to locations of activated RICE devices 190a-e. The presence of a second type of chemical is indicated by the triangles on the map corresponding to locations of activated RICE devices 192a-h. The location of each responding RICE device 190a-e and/or 192a-h represents the presence of chemicals at that location in detection map 130. In one embodiment, such a map 130 could be used by a vehicle in the area to avoid the parts of road 180 with explosives, e.g., to avoid explosives that are present at the locations of RICE devices 190b and 190c, or to determine a new route to its destination that avoids the road 180 altogether. To that end, such a map could be transmitted by the interrogation device to other vehicles in the vicinity of the road 180.

Figure 1C:
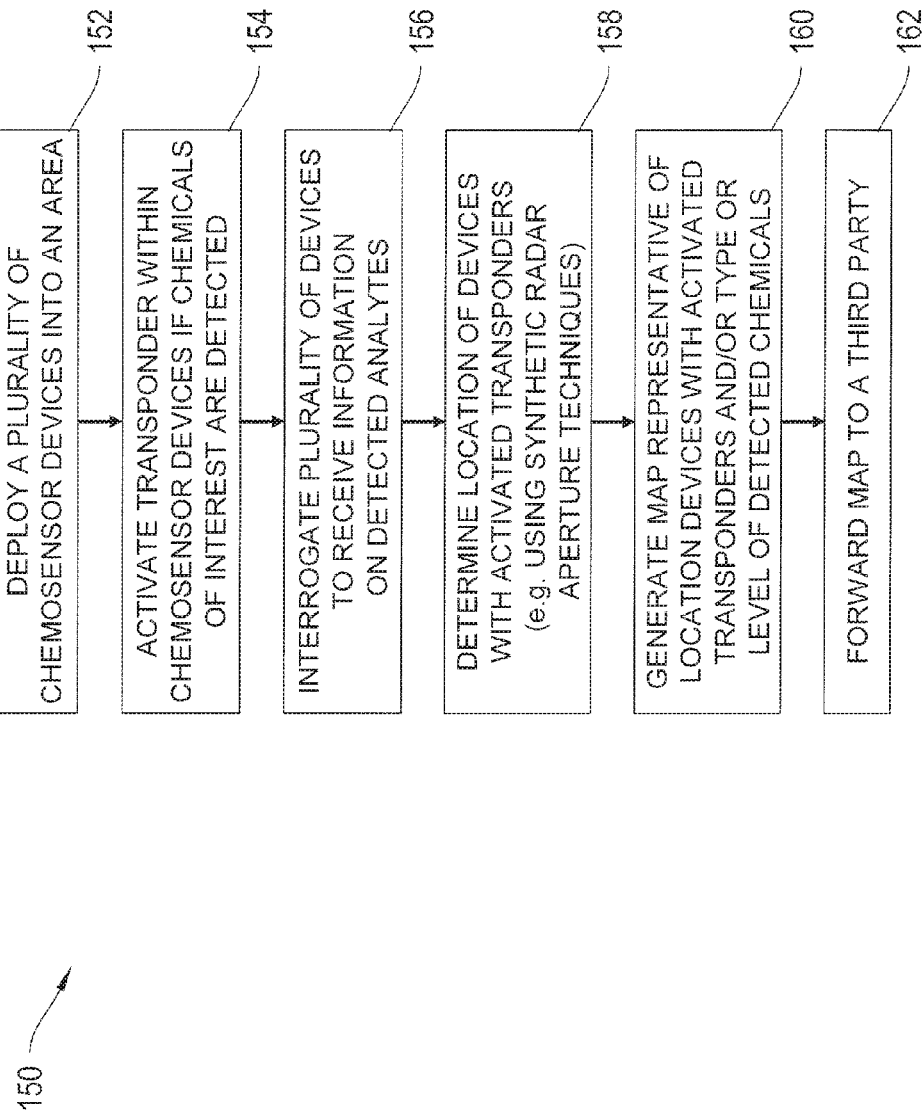
FIG. 1C is a process flow diagram for a method for detecting chemical analytes, according to an illustrative embodiment of the invention.

FIG. 1C illustrates a process flow diagram 150 for a process or method for detecting or sensing chemical analytes used, e.g., to generate the detection map 130 of FIG. 1B. First, a plurality of chemosensor devices (e.g., RICE devices 102 from FIG. 1A) are deployed into an area (step 152). These devices may be deployed by unmanned or manned vehicles, e.g., the UAVs described in relation to FIG. 1A. If chemical analytes are detected by these devices, the transponder within these devices activate (step 154). The devices are then interrogated (e.g., by an interrogation device as described in relation to FIG. 1A) to determine whether any chemicals of interest were detected (step 156). Activated interrogated devices respond with a return signal including, in one embodiment, a code indicative of the analyte detected and/or a concentration level of the analyte. The location of the activated devices is then determined using, e.g., synthetic aperture radar (SAR) techniques (step 158). Information representative of location and/or type of chemicals, e.g., a detection map, may then be generated by the interrogation device (step 160), and this information may be forwarded to a third party (step 162). For example, in a military application, the information may be a map of detected explosives that is forwarded to a convoy or other vehicle allowing this vehicle to avoid any explosives that may be in the vehicle's path. The information may also include codes indicative of the analyte detected or concentration levels of the analyte. In alternative embodiments, the information may also be forwarded to an additional device instead of being transmitted to the interrogation device, and this additional device may generate the detection map.

Figure 2A:
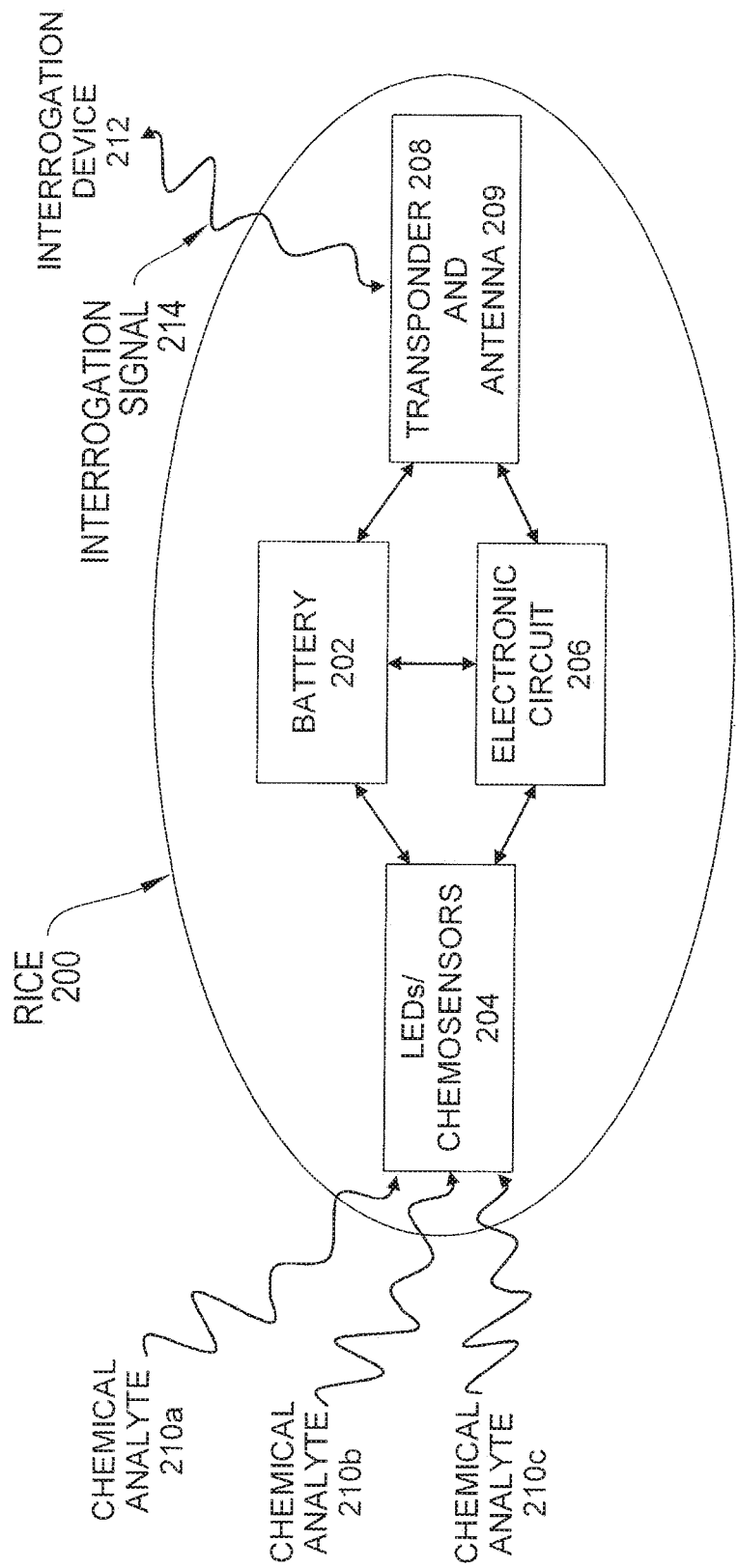
FIG. 2A is a block diagram of a first RICE device, according to an illustrative embodiment of the invention.
Figure 2B:
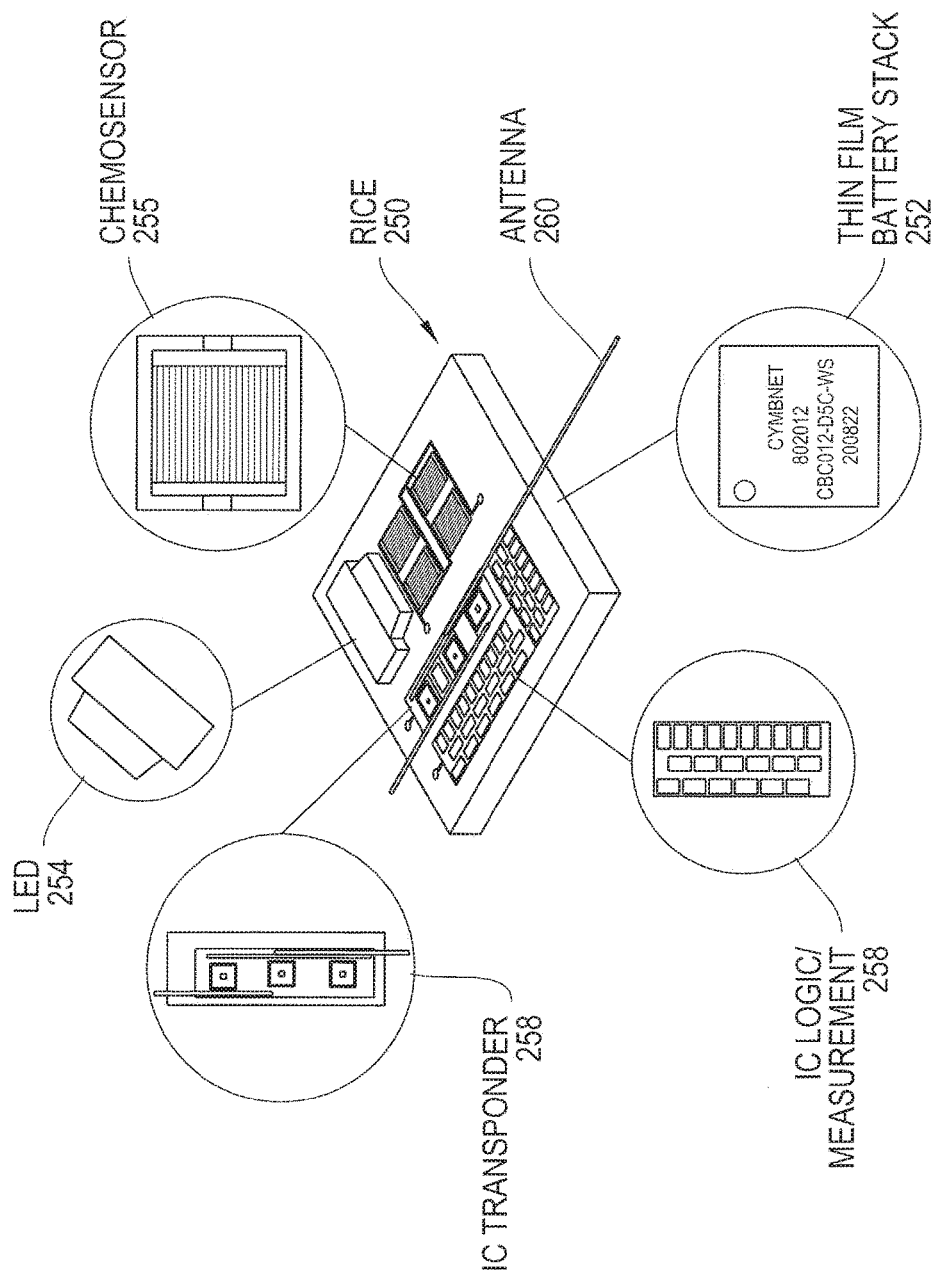
FIG. 2B is a schematic diagram of an implementation of the RICE device of FIG. 2A, according to an illustrative embodiment of the invention.

FIGS. 2A and 2B are illustrations of embodiments of a RICE device 200 and RICE device 250 suitable for use in the application and methodology described above. In some embodiments, a RICE device is fabricated to have a size on the order of that of a grain of rice. For example, a RICE device may have a cross-section area ranging from 0.6 micrometer squared to 1 millimeter squared.

With reference to FIGS. 2A and 2B, RICE device 200 includes a battery 202 which provides power to electronic circuit 206, transponder 208, and LEDs/chemosensors 204, or any combination thereof. Battery 202 may be any suitable thin-film battery that is capable of powering an LED, the components of electronic circuit 206, and the components of the transponder 208. LEDs/chemosensors 204 include one or more LEDs that are capable of illuminating one or more respective chemosensors. The chemosensors themselves include a fluorescent polymer whose fluorescence changes based upon the level of chemicals that bind to the polymer. Examples of such fluorescent polymers are given in U.S. Pat. Nos. 7,208,122 and 7,393,503, the contents of each of which are incorporated herein in their entirety.

RICE device 250 includes an integrated chemosensor 255, LED 254, as well as integrated circuit (IC) radar transponder 258, IC logic and measurement circuitry 256, thin-film battery stack 252 and microfabricated antenna 209 or 260. Each of these components may have millimeter or micrometer dimensions and consume very little power. This low power consumption allows a suitably small-size thin-film battery stack to power the RICE device 200 or 250 for long periods of time. In some embodiments, LED 254 may be a microLED with dimensions 0.2×0.2 by 0.5 mm and a power consumption of 1 mW. The IC circuitry 256 may be an MSP430 microprocessor (available from Texas Instruments, Inc., in Dallas, Tex.) with dimensions 4 mm×4 mm×1 mm, and a power consumption of 350 microwatts. The chemosensor 255 may be a thin-film microfabricated sensor with dimensions of approximately 0.6 mm×1 mm×0.001 mm, and a power consumption of 1 mW. The thin-film battery stack may have dimensions of approximately 8 mm×8 mm×0.17 mm, and a power density of 200 microwatt-hours. Alternatively, RICE device 200 or 250 may use a zinc-air battery. A typical zinc-air battery has a diameter of about 6 mm and a thickness of about 3-4 mm, and a power density of 120 milliwatt-hours.

Those skilled in the art will realize that combinations of the elements in RICE device 200 or 250 may be microfabricated in a stack. For instance, the LED and the chemosensor 204 or 254 and 255, may be formed in two layers of a stack and/or the LED 254 and the chemosensor 255 may be fabricated as a layer on top of the thin-film battery stack 252.

The LEDs/chemosensors may be also be microfabricated or integrated on a chip with up to 4 or 5 chemosensors per RICE device, as shown for RICE device 250. Each chemosensor may detect the same or different chemicals. LED 254 and chemosensors 255 (or LED/chemosensors 204), are in communication with electronic circuit 206 and 256, while electronic circuit 206 and 256 is in communication with transponder 208 and 258, respectively.

As indicated above, the LEDs 204 and 254 radiate the chemosensors 204 and 255 in the RICE device 200 or 250, respectively. If one or more analytes 210a-c are present, the fluorescence of one or more of the chemosensors changes. In one embodiment, this change is detected as a change in electrical current. The electronic circuit 206 or 256 interprets this change in electrical current as indicative of the presence of the chemical analytes as described further below. The relationship between electrical current and the fluorescence of the chemosensors is described further in "Lateral organic bilayer heterojunction photoconductors," published in Appl. Phys. Lett. 93, 063305 (2008)", the contents of which are incorporated herein in their entirety.

Electronic circuit 206 or 256 includes circuitry for detecting the change in electrical current from the LEDs/chemosensors 204, or 254 and 255, circuitry for comparing the detected electrical current to a predetermined threshold electrical current or a prior/historical electrical current, and circuitry for transmitting an electronic signal representative of the comparison to transponder 208 or 258. The predetermined electrical current level(s) may include typical values of electrical current expected to be detected by the circuitry for a particular LED light strength, particular battery power level, and particular chemosensor (i.e., for a particular analyte and polymer or any combination thereof). The prior/historical current values include past values of electrical current detected from the chemosensor and previously stored in memory by the circuitry. In such embodiments, the devices analyze a rate of change of current as opposed to a particular current level. Electronic circuit 206 or 256 also includes other suitable electronic components, e.g., differential amplifiers and comparators for comparing the detected electrical current to the threshold or prior/historical current, processors or other logic circuitry (e.g., an Application Specific Integrated Circuit (ASIC)) for controlling or guiding the operation of the electronic circuit, and memory elements (e.g., ROM, RAM, or EEPROM) for storing, among other things, the threshold current or prior/historical current level(s).

Transponder 208 or 258 includes electronics for receiving and transmitting signals. The electronics includes a receiver for receiving interrogation signals, a transmitter for transmitting signals, and other electronic circuitry. The other electronic circuitry includes a processor 256, for processing the received signals and transmitting signals in response to the received signals, an electronic tag which may be activated by the remote interrogation device 212, or by the electronic circuit 206 or 256 of RICE device 200 or 250, respectively, and an antenna 209 or 260, for receiving interrogation signals and transmitting signals in response to the interrogation signals.

Transponder 208 or 258 is configured to be remotely interrogated by interrogation device 212 via interrogation signal 214. Interrogation device 212 may be deployed in a manned vehicle or UAV such as UAV 101a and/or 101b described in relation to FIG. 1A above. The interrogation signals may range from very-high frequency (VHF) signals to Ka-band signals, or may be RADAR signals. If the interrogation signal 214 is a RADAR signal, transponder 208 or 258 is referred to as a radar transponder.

The electronic tag of the transponder 208 or 258 is activated or "on" if the detected electrical current from the chemosensor, when compared to the threshold electrical current or rate of change in electrical current, signifies the presence of chemicals such as vapor-phase explosives. The electronic tag of the transponder 208 or 258 is deactivated or "off" if the detected electrical current or rate of change of electrical current from the chemosensor signifies the absence (or relative absence) of chemicals.

If interrogation signal 214 is present, and if the electronic tag in transponder 208 or 258 is activated or "on", transponder 208 or 258 transmits a signal representative of the detected electrical current (or presence of chemicals) to interrogation device 212. In one embodiment, the response signal may be a stream of binary numbers, e.g., 000, 010, 011, etc., modulated onto a carrier wave. Each binary number encodes information representative of the detected chemicals. In other embodiments, the response signal is the received signal's frequency, or the received signal's frequency divided by 2. For instance, an activated transponder could receive a signal at a particular frequency, divide the received signal's frequency by 2, and transmit a signal with this halved frequency to the interrogation device. For instance, if the interrogation signal frequency generated by the interrogation device to the transponder is approximately 450 Mhz, transponder 208 or 258 may transmit a signal to the interrogation device at approximately 225 Mhz. In general, the transponder 208 or 258 and interrogation device may use any suitable transmission frequency for the signal, e.g., ranging from a few MHz to several GHz.

The transmitted signal from the RICE device transponder 208 or 258 allows the interrogation device to determine from the received signal (1) the location of the RICE device 200 or 250 and (2) the presence of chemicals at that location. In one embodiment, device localization is performed using a synthetic aperture radar (SAR) image formation technique. With this approach, a "heat map" of the ground is generated such that, e.g., bright pixels correspond to RICE devices which are activated and have detected a chemical of interest. SAR processing algorithms enable resolutions (i.e., RICE device/analyte location accuracies) of 1 ft or better.

In one embodiment, the transponder 208 or 258 may be remotely interrogated from distances of a few meters up to 15 km. In another embodiment, the remote interrogation distance may be between approximately 250 m and approximately 10 km. Those skilled in the art may alter this "stand-off" distance by appropriately sizing the transponder receiver and transmitter, as well as the antenna on the interrogation device. Such a design may involve the use of a RADAR system design equation that relates the design of the transponder (e.g., receiver size, antenna size, transmission power, transmission energy, etc.) to the stand-off distance. A radar transponder generally has a range of a few meters to 15 km, e.g., 250 m, and consumes approximately 1 mW of transmission power.

As described below with respect to FIG. 3, radar transponders can be microfabricated to have a cross-section area of roughly 2.5 square millimeters (e.g., 0.75 mm×3.25 mm×0.25 mm), and use much less power—approximately 10 mW—than other types of transponders. In contrast to radar transponders, state of the art passive radio frequency ID (RFID) tags have a range that of roughly 20 meters, and a size of approximately 4 square millimeters, and consume much more power than a radar transponder. Active RFID tags are typically even larger (e.g., 85 mm×54 mm×4.5 mm) and consume even more power than passive RFID tags, though they have a range of about 200 meters.

Figure 3:
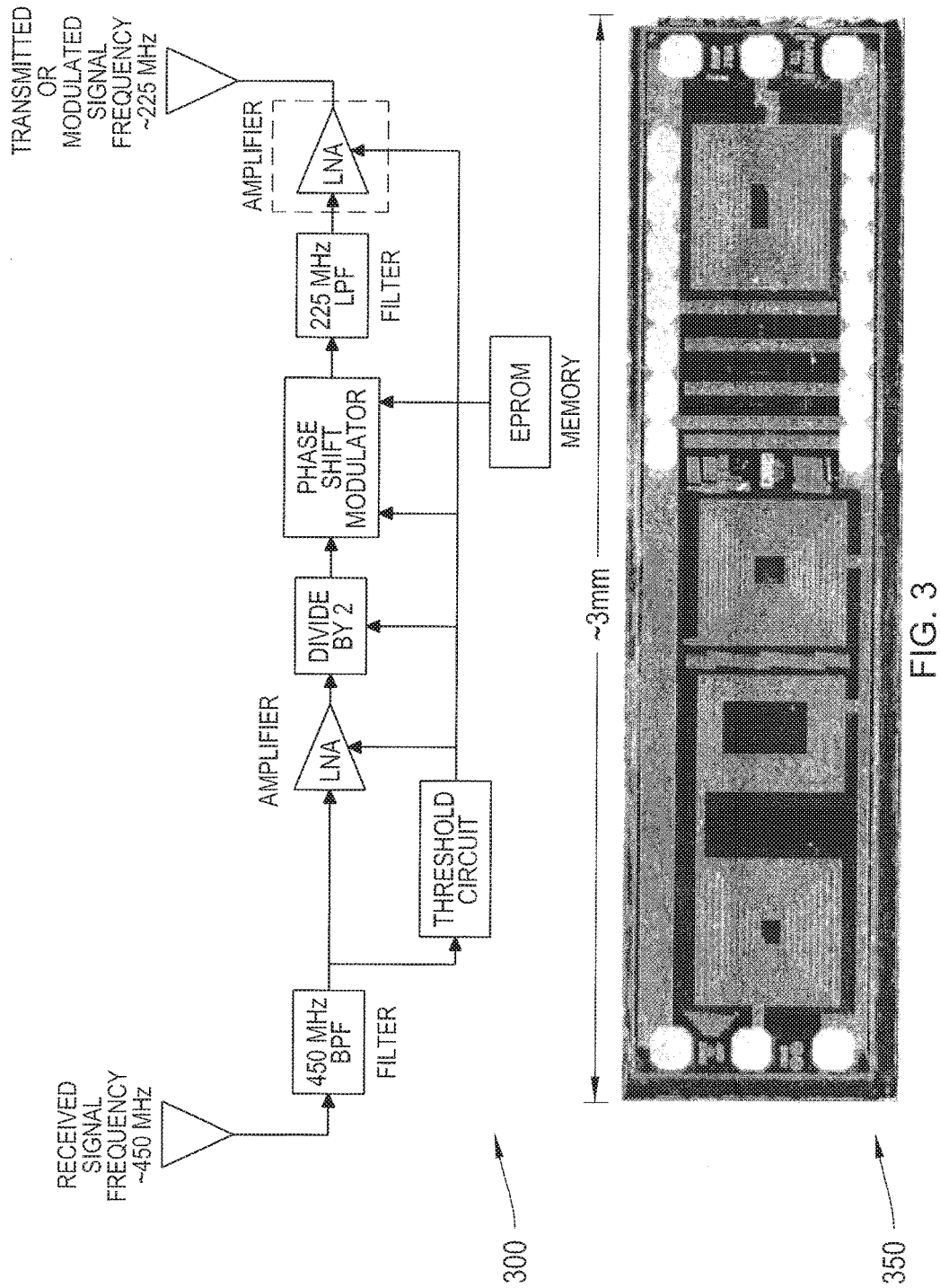
FIG. 3 is an architecture block diagram and a picture of an integrated circuit of a transponder for use in a RICE device such as the RICE devices of FIGS. 2A and 2B, according to an illustrative embodiment.

FIG. 3 illustrates a block diagram 300 of a divide-by-2 transponder architecture along with a photograph of an IC implementing a RICE device transponder for an embodiment of the RICE device transponder, such as transponders 208 or 258 in FIGS. 2A and 2B, respectively. The transponder receives an interrogation signal with frequency ~450 MHz. The transponder subsequently filters (e.g., using a 450 MHz Band Pass Filter (BPF)) and amplifies (e.g., using a Low-Noise Amplifier (LNA)) this signal. The filtered and amplified signal is then passed through a divide-by-two digital electronic circuit. In some embodiments, the signal can be phase-shift modulated. After the division-by-two and/or modulation stages, the resulting signal is filtered (e.g., using a 225 MHz Low Pass Filter (LPF)), amplified (e.g., using a Low-Noise Amplifier (LNA)) and transmitted to the interrogation device.

This divide-by-2 transponder block diagram architecture 300 provides sufficient isolation between transmit and receive to keep the device from self-oscillating. The transponder's transmitted signal is coherent, i.e., of the same phase as the interrogation signal, thereby allowing the interrogation device to coherently process the transmitted signal to determine both the range and cross-range components of the RICE device's location. Transponder architecture 300 can be microfabricated, e.g., on BiCMOS SiGe, to have sizes of less then 3 square millimeters as shown in integrated circuit 350. Depending on the signal frequencies, such a transponder can be miniaturized even further. That is, at higher frequencies, the electronic components may be made even smaller.

With continued reference to FIGS. 2A, 2B and 3, the battery lifetime of transponder 208, 258 (and thus, RICE device 200 or 250) is generally limited by the power consumption of the low noise amplifier (LNA). While very low power amplifiers (with power consumptions of less than approximately 1-10 mW) are suitable for this application, operating even LNAs continuously could limit the endurance of the device to a few hours if only low power density thin-film batteries 202 or 252 are used. In some embodiments, sleep cycling techniques can be applied to the processor of transponder 208 or 258 to significantly extend the endurance of the device, to several weeks or longer. These techniques use very low-power (with power consumptions of less than tens of microwatts) clocks and digital logic circuitry that typically energize the amplifier only at points in time when the device is responding to the interrogation device 212.

Additionally, or alternatively, prolonged battery lifetimes for transponder 208 or 258 may be obtained by using an interrogation device 212 with significant power density incident at the transponder 208 or 258. This generally requires either higher interrogation device 212 transmission power, greater interrogation device 212 antenna gain, or shorter standoff ranges for interrogation. For instance, sufficient power density incident at the transponder 208 or 258 allows the interrogation device 212 to more directly awaken transponder without requiring the amplifier (e.g., LNA) to be awakened from a sleep cycle.

Figures 4A, 4B:
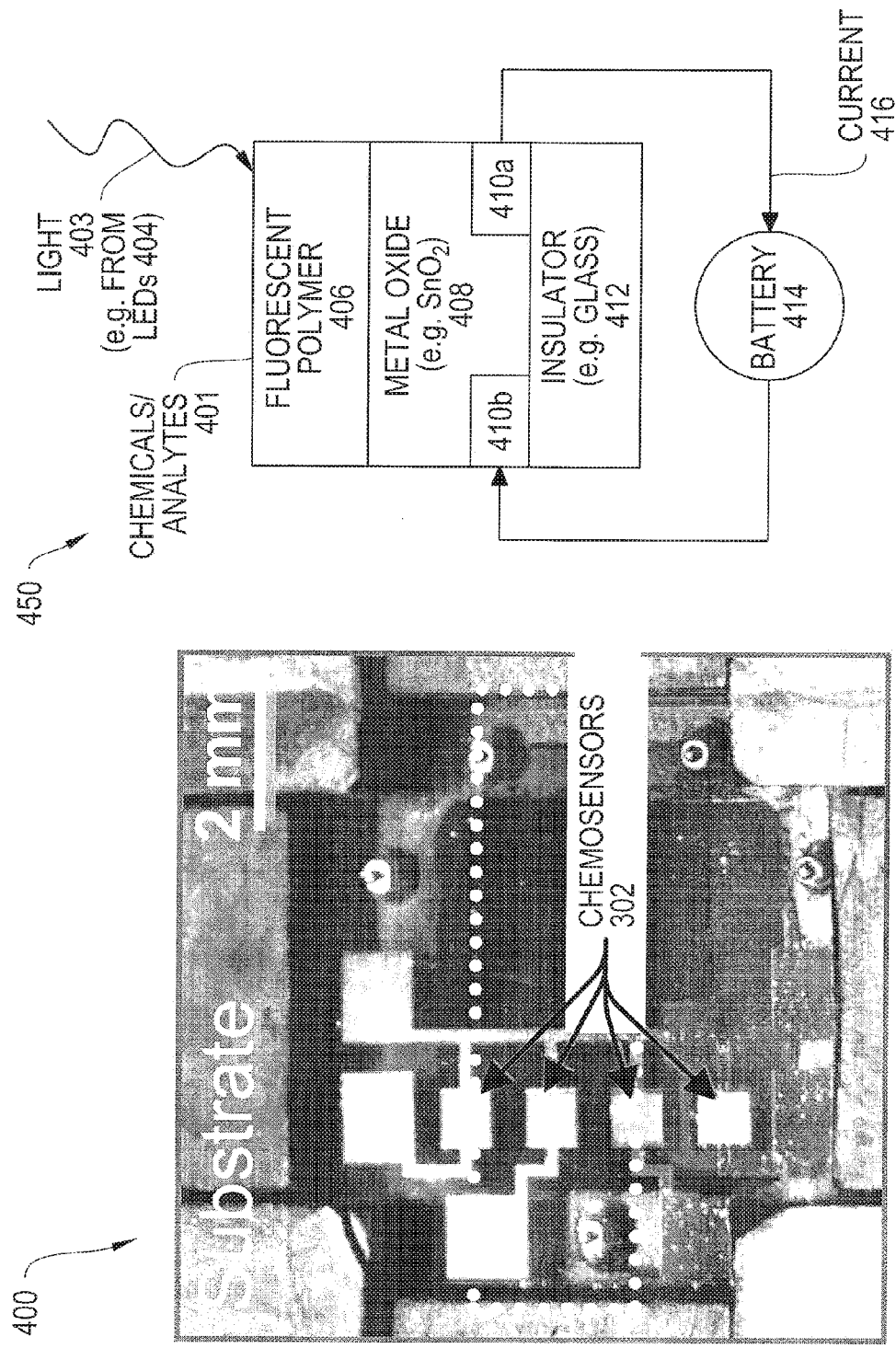
FIG. 4A is a picture of a microfabricated chemosensor chip for use in a RICE device such as the RICE devices of FIGS. 2A and 2B that includes multiple chemosensors, according to a first illustrative embodiment.
FIG. 4B is a schematic of a chemosensor for use in a RICE device such as the RICE devices of FIGS. 2A and 2B or in a chemosensor chip such as the chip of FIG. 4A, according to a second illustrative embodiment.

FIG. 4A shows an illustration of a microfabricated chemosensor chip 400, including a plurality of chemosensors 402 for detecting or sensing chemical analytes. Chemosensor chip 400 could be a component of RICE devices 200 or 250 described above with respect to FIGS. 2A and 2B. The chemosensors 402 have micrometer-scale dimensions, and are illuminated by one or more LED light sources (not shown). In some embodiments, the LEDs may be microLEDs. The combination of a microLED with a chemosensor chip 300 may be part of a RICE device such as LED/chemosensors 204 in RICE device 200 in FIG. 2A. This implementation is discussed further with respect to FIG. 4C.

FIG. 4B shows a block diagram of a chemosensor 450. Such a chemosensor, is similar to the chemosensors 402 illustrated in FIG. 4A above and includes a Type-II bilayer heterojunction. This bilayer heterojunction includes a fluorescent polymer layer 406 and a metal oxide layer 408, e.g., $SnO_2$. The Type-II bilayer heterojunction itself is deposited on planar electrodes 410a and 410b that enable the application of an electric field to the heterojunction using a battery 414. The heterojunction also includes an insulating layer 412 such as glass. Further description of Type-II bilayer heterojunctions may be found in Chapter 6 of "Organic Lateral Heterojunction Devices for Vapor-phase Chemical Detection", a Ph.D. Thesis by John Ho, published by the Massachusetts Institute of Technology in June 2009. The contents of this document, including Chapter 6, are hereby incorporated herein in their entirety.

In one embodiment, the Type-II bilayer heterojunction is constructed by spin-casting a fluorescent polymer that is sensitive to a particular explosive on top of a second, more conductive thin film metal oxide layer. Thus, the sensors themselves are capable of miniaturization and on-chip integration with other microfabricated structures, e.g., with transponder 350 (FIG. 3). Furthermore, the resulting micrometer dimensions allow for close-packed, multiplexed LED/chemosensor chips, e.g., 400 in FIG. 4A that can detect a wide range of chemical analytes.

Figure 4C:
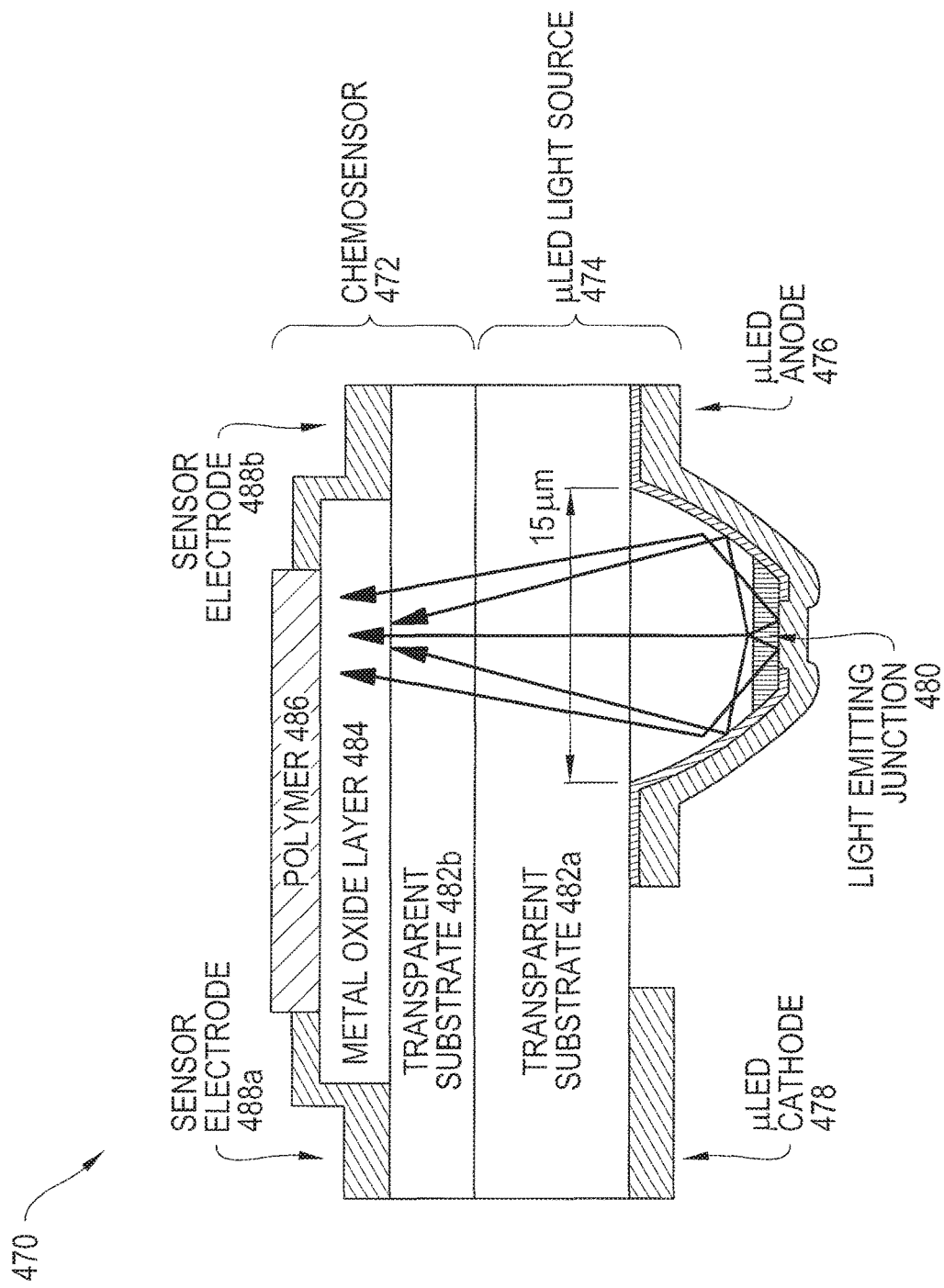
FIG. 4C is a schematic of a microfabricated chemosensor with a microLED for use in a RICE device such as the RICE devices of FIGS. 2A and 2B or in a chemosensor chip such as the chip of FIG. 4A, according to a third illustrative embodiment.

FIG. 4C shows a schematic of a chemosensor with a microLED structure 470. MicroLEDs are small in size, making them suitable for microfabrication and inclusion into the RICE devices discussed herein. For instance, microLEDs may be integrated with other microelectronic circuit such as a microprocessor, amplifier, ASIC, or field-programmable gate array (FPGA). Structure 470 includes a chemosensor 472 and microLED light source 474. The microLED light source 474 includes an anode 476 and a cathode 478, which are on either side of light emitting junction 480. Light from LED light source 474 passes through transparent substrate 482a before reaching transparent substrate 482b of chemosensor 472. Chemosensor 472 also includes sensor electrodes 488a and 488b, metal oxide layer 484, and fluorescent polymer 486. The fluorescence of the polymer 486 changes based on the chemical analytes the structure 470 is exposed to, and this change in fluorescence is sensed as a change in resistance, and effectively, a change in the voltage or current sensed across electrodes 488a and 488b.

Figure 5A:
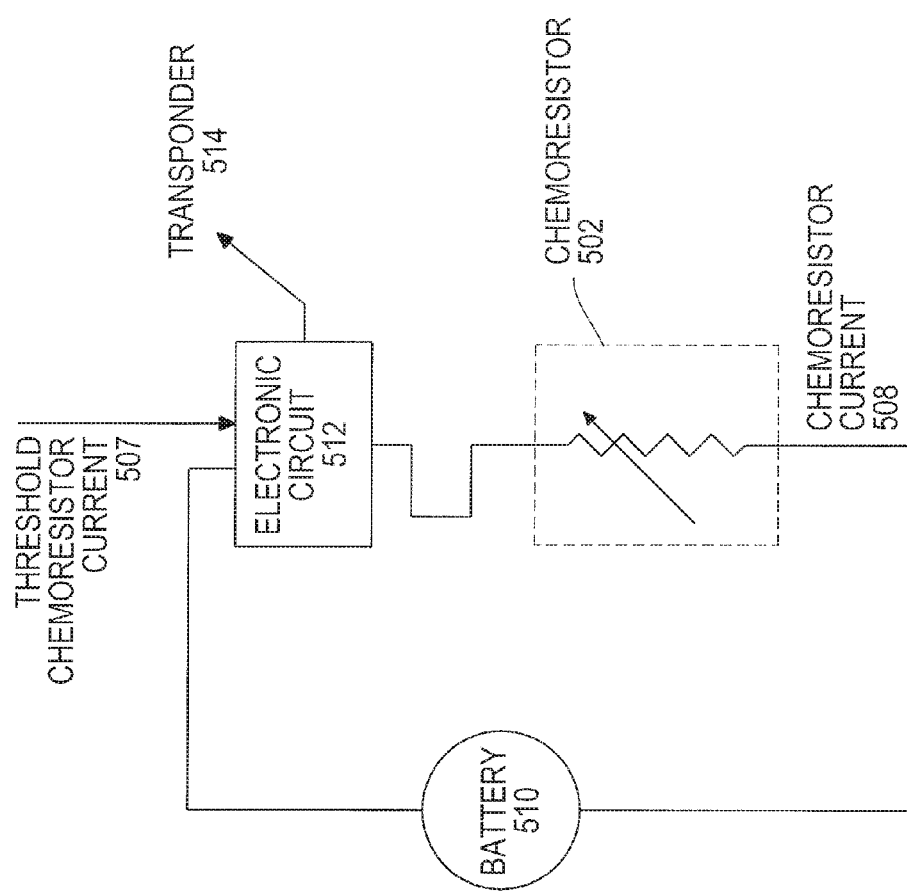
FIG. 5A is an abstraction of the bilayer heterojunction structure of an electrical circuit of a chemosensor of a RICE device such as the chemosensors in FIGS. 4A-4C, according to an illustrative embodiment.

FIG. 5A illustrates an abstraction of the bilayer heterojunction structure to an electrical circuit. Battery 510 provides for an electric field across an LED/chemosensor chip, shown in the figure as a variable chemoresistor 502. The effective resistance of chemoresistor 502 is dependent upon the level of LED light irradiating the chemosensor from the LED, the temperature of the Type-II bilayer heterojunction, the level of chemicals attached to the fluorescent polymer, and the strength of the electric field applied by battery 510. Effectively, this chemosensor has a tunable dynamic range which can be adjusted by changing operating conditions (battery voltage, temperature, etc.) to make the sensors more or less sensitive to a particular chemical/analyte.

Figure 5B:
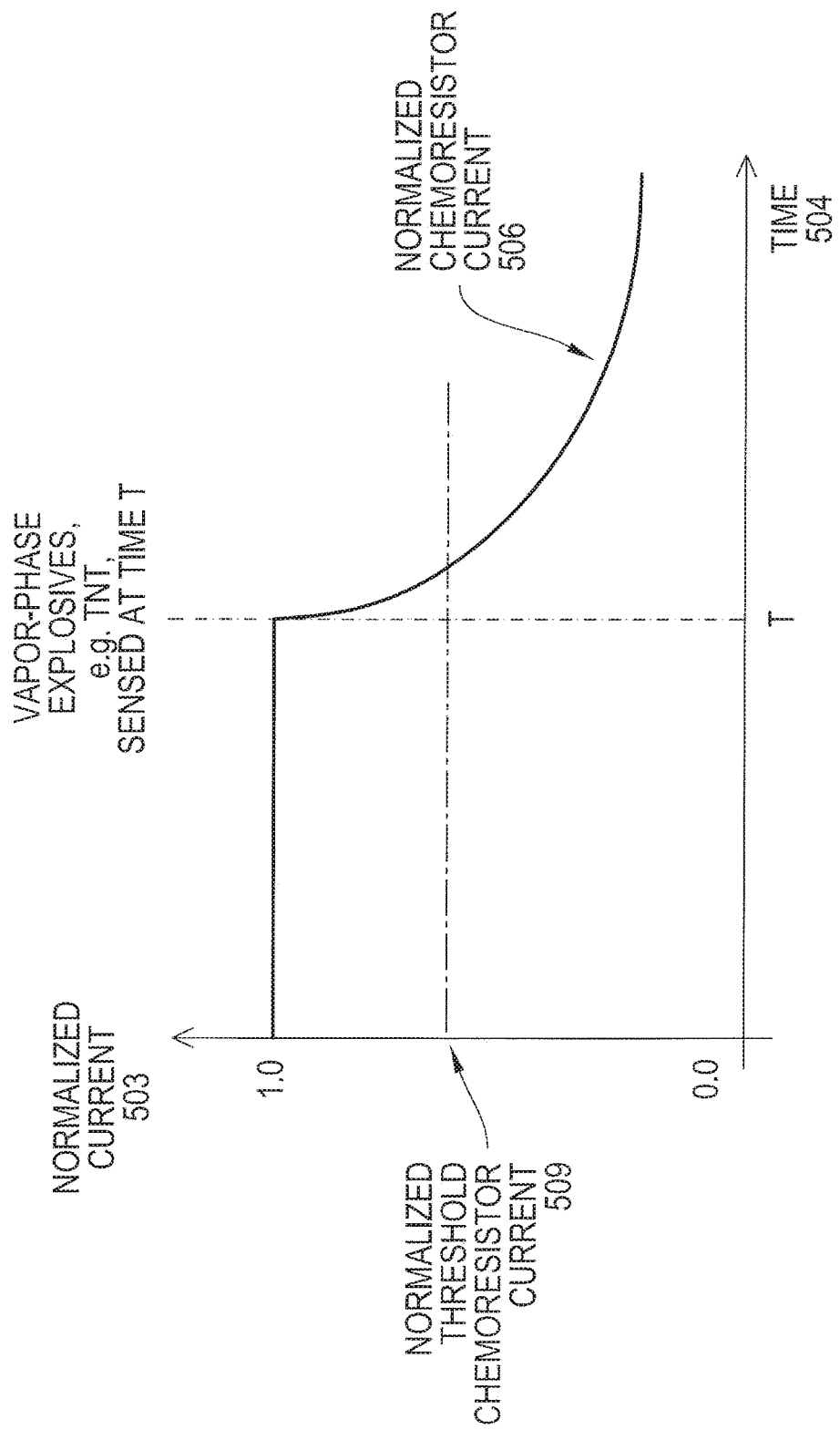
FIG. 5B is a graph of normalized current versus time for a vapor-phase explosives detection application of a RICE device such as the RICE devices of FIGS. 2A and 2B, according to an illustrative embodiment.

FIG. 5B illustrates a graph of normalized current 503 versus time 504 for a vapor-phase explosives detection application. At Time=T, vapor-phased explosives are attached to a fluorescent polymer in the Type-II bilayer heterojunction structure. As more explosives attach to the fluorescent polymer, the resistance of the chemoresistor 502 becomes large, resulting in an exponentially-decaying normalized chemoresistor current 506. The exponentially-decaying waveform may have a different morphology if a different fluorescent polymer is used in the bilayer heterojunction. In one embodiment, if electronic circuit 512 senses that the value of the normalized chemoresistor current 506 is less than the value of the threshold chemoresistor current 509, electronic circuit 512 transmits the signal to transponder 514. The comparison of the two currents may be performed using any suitable electronic means, e.g., a differential amplifier, or a comparator circuit. The transponder may then transmit information to a remote interrogation device as described above in relation to FIGS. 1A-2B. In an alternative embodiment, a signal is only sent to the transponder when a rate of change of current passes a threshold rate that is determined based on a prior current level.

Figure 6:
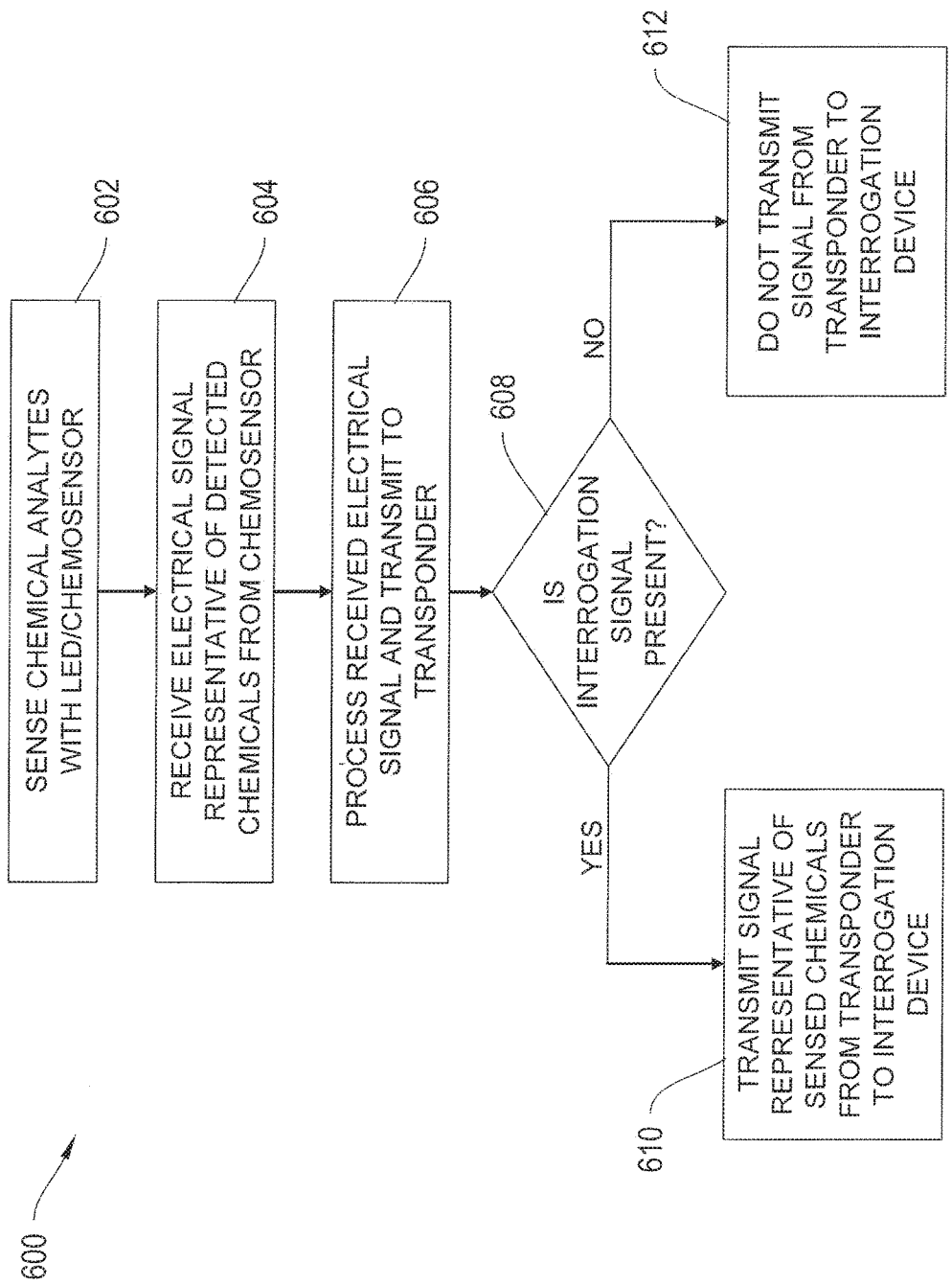
FIG. 6 is a process flow diagram for a method for detecting chemical analytes using RICE device such as the RICE devices of FIGS. 2A and 2B, according to an illustrative embodiment.

FIG. 6 illustrates a process flow diagram 600 for a process or method for detecting chemical analytes. Chemicals are first sensed using an LED/Chemosensor (step 602). The LED/Chemosensor may be implemented as described above in relation to FIGS. 4A-4C. The electrical signal, e.g., a current, from the chemosensor is received by the electronic circuit (step 604). This circuit may be implemented as described in relation to electronic circuit 512 (FIG. 5A).

The received electronic signal is then processed by the electronic circuit (step 606). For instance, the electronic circuit may compare the received electrical current signal to a threshold electrical current or prior/historical current level (s) stored in a memory device in the electronic circuit, and transmit the results of this comparison as a second electrical signal to a transponder. Or as described above, the electronic circuit may compare the rate of change of the electrical current to a threshold determined based on a prior current level.

If an interrogation signal is received by the transponder from a remote interrogation device (step 608), then the transponder of the device, if it had detected a chemical of interest, transmits a signal representative of the sensed chemical to the remote interrogation device (step 610). On the other hand, if an interrogation signal is not received, the transponder does not transmit a signal (step 612).

There are several advantages achieved by the various embodiments described herein with respect to FIGS. 1A-6B. Among other advantages, with microfabricated photoconductive sensors which are electrically isolated and integrated with microfabricated transponders, the chemical detection device can be miniaturized, deployed in large numbers, and can be interrogated remotely from substantial distances.

The invention may be embodied in other specific forms without departing from the spirit or essential characteristics thereof. The forgoing embodiments are therefore to be considered in all respects illustrative, rather than limiting of the invention.

The invention claimed is:

1. A method for detection and localization of chemical analytes, comprising:
deploying a plurality of devices, each device comprising a chemosensor and a transponder, in an area to detect a chemical analyte;
simultaneously transmitting an interrogation signal to the plurality of devices;
activating the transponder of each of a subset of the plurality of devices to transmit a respective return signal responsive to detection of a presence of the chemical analyte and receipt of the interrogation signal by the respective device, the subset including at least two devices;
receiving the respective return signal from each of the subset of the plurality of devices, each respective return signal indicating the presence of the chemical analyte; and
determining a physical location of each of the subset of the plurality of devices based on the respective received return signal.

2. The method of claim 1, wherein determining the physical location of each of the subset of the plurality of devices comprises processing the received return signals of the subset of the plurality of devices using a synthetic aperture radar (SAR) image formation algorithm.

3. The method of claim 1, further comprising generating for display a map of the physical location of each of the subset of the plurality of devices.

4. The method of claim 3, wherein the map visually distinguishes between the physical locations of the subset of the plurality of devices and a remainder of the plurality of devices.

5. The method of claim 1, wherein receiving the respective return signal from each of the subset of the plurality of devices comprises simultaneously receiving the return signal from each of the subset of the plurality of devices.

6. The method of claim 1, further comprising forwarding the determined physical locations to a third party.

7. The method of claim 1, wherein simultaneously transmitting the interrogation signal to the plurality of devices comprises broadcasting the interrogation signal using radar.

8. The method of claim 1, wherein each of the plurality of devices is configured to compare an output signal from the chemosensor to at least one of a threshold signal value and a plurality of prior output signal values stored in a memory to determine the presence of the chemical analyte.

9. The method of claim 1, wherein the return signal includes information on a type of the chemical analyte detected by the respective device.

10. The method of claim 1, wherein the return signal includes information on a concentration level of the chemical analyte detected by the respective device.

11. A system for detection and localization of chemical analytes, comprising:
a plurality of devices, each device comprising a chemosensor, a battery, and a transponder, deployed in an area to detect a chemical analyte; and
a remote interrogation device comprising processing circuitry, the remote interrogation device configured to:
simultaneously transmit an interrogation signal to the plurality of devices;
receive a return signal from each of a subset of the plurality of devices indicating a presence of the chemical analyte, the subset including at least two devices, wherein each respective return signal is transmitted using the transponder of a respective device that is activated to transmit the respective return signal in response to detection of the presence of the chemical analyte and receipt of the interrogation signal; and
determine a physical location of each of the subset of the plurality of devices based on the respective received return signal.

12. The system of claim 11, wherein the remote interrogation device is further configured to determine the physical location of each of the subset of the plurality of devices by processing the received return signals of the subset of the plurality of devices using a synthetic aperture radar (SAR) image formation algorithm.

13. The system of claim 11, wherein the remote interrogation device is further configured to generate for display a map of the physical location of each of the subset of the plurality of devices.

14. The system of claim 13, wherein the map visually distinguishes between the physical locations of the subset of the plurality of devices and a remainder of the plurality of devices.

15. The system of claim 11, wherein the remote interrogation device is further configured to receive the respective return signal from each of the subset of the plurality of devices by simultaneously receiving the return signal from each of the subset of the plurality of devices.

16. The system of claim 11, wherein the remote interrogation device is further configured to forward the determined physical locations to a third party.

17. The system of claim 11, wherein the remote interrogation device is further configured to simultaneously transmit the interrogation signal to the plurality of devices by broadcasting the interrogation signal using radar.

18. The system of claim 11, wherein each of the plurality of devices is configured to compare an output signal from the chemosensor to at least one of a threshold signal value and a plurality of prior output signal values stored in a memory to determine the presence of the chemical analyte.

19. The system of claim 11, wherein the return signal includes information on a concentration level of the chemical analyte detected by the respective device.

20. The system of claim 11 wherein the chemosensor includes a fluorescent polymer.

\* \* \* \* \*